United States Patent
De Haan et al.

(10) Patent No.: US 10,667,704 B2
(45) Date of Patent: Jun. 2, 2020

(54) APPARATUS AND METHOD FOR MEASURING THE QUALITY OF AN EXTRACTED SIGNAL

(71) Applicant: KONINKLIJKE PHILIPS N.V., Eindhoven (NL)

(72) Inventors: Gerard De Haan, Helmond (NL); Albertus Cornelis Den Brinker, Eindhoven (NL); Vincent Jeanne, Migne Auxances (FR); Gerrit Maria Kersten, Veldhoven (NL); Murtaza Bulut, Eindhoven (NL); Michel Jozef Agnes Asselman, Nuenen (NL)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 16/063,507

(22) PCT Filed: Dec. 23, 2016

(86) PCT No.: PCT/EP2016/082554
§ 371 (c)(1),
(2) Date: Jun. 18, 2018

(87) PCT Pub. No.: WO2017/109169
PCT Pub. Date: Jun. 29, 2017

(65) Prior Publication Data
US 2018/0368707 A1      Dec. 27, 2018

(30) Foreign Application Priority Data
Dec. 23, 2015 (EP) .................................... 15202330

(51) Int. Cl.
*A61B 5/024*   (2006.01)
*A61B 5/00*    (2006.01)
(Continued)

(52) U.S. Cl.
CPC ........ *A61B 5/02416* (2013.01); *A61B 5/0077* (2013.01); *A61B 5/0816* (2013.01);
(Continued)

(58) Field of Classification Search
CPC . A61B 5/02416; A61B 5/7257; A61B 5/0816; A61B 5/0077; A61B 5/7246;
(Continued)

(56) References Cited

U.S. PATENT DOCUMENTS

| 7,567,833 B2 | 7/2009 | Moctezuma De La Barrera et al. |
| 2004/0138540 A1 | 7/2004 | Baker, Jr. et al. |

(Continued)

FOREIGN PATENT DOCUMENTS

| WO | 2013156908 A1 | 10/2013 | |
| WO | WO-2014020463 A1 * | 2/2014 | ......... A61B 5/02433 |
| WO | 2015055709 A1 | 4/2015 | |

OTHER PUBLICATIONS

A. V. Moco, S. Stuijk, and G. de Haan, "Ballistocardiographic micro-motion as a threat to remote-PPG imaging", Paper submitted to IEEE tr. on Biomedical Engineering.

(Continued)

*Primary Examiner* — Casey L Kretzer

(57) ABSTRACT

There is provided a system and method of assessing the quality of the extraction of the signal and the reliability of the physiological measurement by providing a system for producing a quality metric for physiological information extraction from a sequence of image frames, the system comprising a signal extraction unit configured to extract a signal representative of a physiological characteristic from a plurality of the image frames, a signal analyzer configured to calculate a plurality of physiological information results from the signal using a plurality of calculation functions, the plurality of calculation functions being comprised within a (Continued)

list of calculation functions, each physiological information result being calculated using a different calculation function, and a quality metric calculator for calculating a quality metric value based on a signal analysis metric derived from a comparison between the physiological information results of the plurality of physiological information results.

14 Claims, 4 Drawing Sheets

(51) Int. Cl.
  *A61B 5/08* (2006.01)
  *G06T 7/00* (2017.01)
(52) U.S. Cl.
  CPC .......... *A61B 5/7207* (2013.01); *A61B 5/7221* (2013.01); *A61B 5/7246* (2013.01); *A61B 5/7257* (2013.01); *G06T 7/0016* (2013.01); *G06T 2207/10024* (2013.01); *G06T 2207/30076* (2013.01)
(58) Field of Classification Search
  CPC ..... A61B 5/7221; A61B 5/7207; G06F 19/00; G06T 7/0016; G06T 2207/30076; G06T 2207/10024
  See application file for complete search history.

(56) References Cited

U.S. PATENT DOCUMENTS

| | | |
|---|---|---|
| 2009/0082642 A1* | 3/2009 | Fine .................... A61B 5/0059 600/300 |
| 2014/0031696 A1 | 1/2014 | Schmeitz et al. |
| 2014/0148663 A1 | 5/2014 | Bresch et al. |
| 2014/0155759 A1 | 6/2014 | Kaestle et al. |
| 2014/0180132 A1 | 6/2014 | Shan et al. |
| 2014/0275832 A1 | 9/2014 | Muehlsteff et al. |
| 2014/0303454 A1 | 10/2014 | Clifton et al. |
| 2015/0031965 A1* | 1/2015 | Visvanathan ........ A61B 5/0059 600/301 |
| 2015/0037781 A1 | 2/2015 | Breed et al. |
| 2015/0057554 A1* | 2/2015 | Watson ............. A61B 5/02125 600/485 |
| 2015/0105670 A1 | 4/2015 | Bresch et al. |
| 2015/0176971 A1 | 6/2015 | Buckland |
| 2015/0297142 A1* | 10/2015 | De Jaam ............ G06K 9/00503 600/407 |

OTHER PUBLICATIONS

Tarassenko, L. et al., "Non-contact video-based vital sign monitoring using ambient light and auto-regressive models", 2014, pp. 807-831.

* cited by examiner

APPARATUS AND METHOD FOR MEASURING THE QUALITY OF AN EXTRACTED SIGNAL

CROSS-REFERENCE TO PRIOR APPLICATIONS

This application is the U.S. National Phase application under 35 U.S.C. § 371 of International Application No. PCT/EP2016/082554, filed on 23 Dec. 2016, which claims the benefit of European Patent Application No. 15202330.5, filed on 23 Dec. 2015. These applications are hereby incorporated by reference herein.

FIELD OF THE INVENTION

The present invention relates to the extraction of periodic signals from other data, particularly the extraction of signals representing physiological characteristics from video sequences.

BACKGROUND

It is possible to analyze video sequences of a living subject and detect small changes in the images which are the result of physiological processes of that subject. Amongst these physiological process are such things as blood flow, breathing and sweating.

Certain physiological processes can be observed via skin reflectance variations. The human skin can be modelled as an object with at least two layers, one of those being the epidermis (a thin surface layer) and the other the dermis (a thicker layer underneath the epidermis). A certain percentage 5% of an incoming ray of light is reflected at the skin surface. The remaining light is scattered and absorbed within the two skin layers in a phenomenon known as body reflectance (described in the Dichromatic Reflection Model). The melanin, typically present at the boundary of epidermis and dermis, behaves like an optical filter, mainly absorbing light. In the dermis, light is both scattered and absorbed. The absorption is dependent on the blood composition, so that the absorption is sensitive to blood flow variations. The dermis contains a dense network of blood vessels, about 10% of an adult's total vessel network. These vessels contract and expand according of the blood flow in the body. They consequently change the structures of the dermis, which influences the reflectance of the skin layers.

Other physiological processes such as breathing cause movement in the surface of patient.

Other physiological processes such as variations in blood oxygenation level can manifest themselves as small colour changes.

It is possible to detect and extract signals which have some periodic content in these changes and from that obtain a result such as a frequency in the case of periodic processes. For example, a subject may be illuminated with ambient light and filmed using a video camera. By analyzing changes in the values of corresponding pixels between frames of the sequence of images, a time-variant signal can be extracted. This signal may be transformed into frequency-like domain using something like a Fast Fourier Transform and from the frequency-domain spectra, a value for the subject's heart-rate may be arrived at as a physiological measurement. These physiological measurements are often called vital signs.

The changes in the pixel values are often small and often more pronounced in 1 colour channel than the others. Thus the signal that is being looked for is correspondingly small.

There may be other changes in the pixel values such as those due to changes in the general image and these can be comparatively large. There are also sources of random change in the pixel values such as noise in the image sensor and variations in the illumination (such as flicker). All of these are, to all intents and purposes, uncorrelated with the signal being sought. Therefore the signal to noise ratio is small and the physiological measurement may be sometimes of questionable reliability.

SUMMARY OF THE INVENTION

Therefore it is desirable to provide a method of assessing the quality of the extraction of the signal and the reliability of the physiological measurement by providing a system for producing a quality metric for physiological information extraction from a sequence of image frames, the system comprising a signal extraction unit configured to extract a signal representative of a physiological characteristic from a plurality of the image frames, a signal analyzer configured to calculate a plurality of physiological information results from the signal using a plurality of calculation functions, the plurality of calculation functions being comprised within a list of calculation functions, each physiological information result being calculated using a different calculation function, and a quality metric calculator for calculating a quality metric value based on a signal analysis metric derived from a comparison between the physiological information results of the plurality of physiological information results. This offers the advantage that the degree to which the results of the different calculation functions agree can be an indication of the extracted signal quality, and hence the image processing that contributed to it, can be derived.

According to an embodiment, the list of calculation functions comprises an autocorrelation function, a Fourier transform function, a power spectral density function and a Laplace transform. These have the advantage of having slightly different characteristics and sensitivities. Therefore the degree of agreement may be a useful indication of the quality of the overall process.

According to an embodiment, the system of any preceding claim further comprises an illumination quality assessor configured to produce illumination value indicative of an amplitude of the signal. This has the advantage that along with the general assessment of the process provided by the 'comparison of analysis methods', the quality metric has sensitivity to the illumination quality and can be used by the user to adjust the illumination.

According to an embodiment, the system further comprises a motion compensation assessor configured to produce a motion compensation metric derived from at least one of a variation in the amplitude of the signal and compensation metric derived from a displacement vector representative of the relative motion of an image feature between image frames in the plurality of image frames. This has the advantage that along with the general assessment of the process provided by the 'comparison of analysis methods', the quality metric has sensitivity to the motion compensation quality. The quality metric could be used either by the user to adjust the system settings or to stabilize the subject or encourage them to move less. Another possibility is that the quality metric could be used by the controller to control the settings of the signal extraction unit.

According to an embodiment, the system further comprises an illumination angle assessor configured to produce an illumination angle metric derived from a measurement of reflected illumination levels. The system can measure the degree to which oblique illumination is affecting the results in a number of ways. The system may contribute to an illumination quality metric by using an illumination angle assessor to measure the illumination homogeneity or angle from reflected illumination levels. This has the advantage of being more sensitive to defects or problems that are the result of the set-up or environment of the overall system.

According to an embodiment, the illumination angle metric is based on at least one of a histogram of pixel values, a standard deviation, a variance of pixel values, measurements of gradients in said pixel values across the area of interest and a reading from a directional photodiode. This histogram is similar in information content to calculations already needed for the signal processing and so may be implemented easily as part of the quality metric in a similar manner. This may be a more precise indication of the illumination quality than histogram and the advantage of including a more precise is that it can then be used to generate feedback that can instruct the user how to improve the set-up.

According to an embodiment, the system of any of preceding claim configured to calculate the quality metric value based on a combination of at least two of a signal comparison metric, an illumination quality metric, a motion compensation metric and an illumination homogeneity metric. The advantage of directional photodiodes is that they are relatively inexpensive and can be placed and oriented to take into account the actual situation.

According to an embodiment, The system of any preceding claim configured to compare quality metric values to a first chosen limit over a chosen time period and record a pass-fail result and compare the number of pass-fail results in the chosen time period to second chosen limit in order to produce a derived quality metric for the chosen time period.

According to an embodiment, the system of any of the preceding claims configured to provide an indication of the quality of the extracted physiological information.

In another aspect, there is provided a method of producing a quality metric for an extraction of a physiological information result comprising extracting a signal representative of a physiological characteristic, calculating a plurality of physiological information results from the signal using a plurality of calculation functions, the plurality of calculation functions being comprised within a list of calculation functions, each physiological information result being calculated using a different calculation function, and calculating a quality metric based on a comparison between the physiological information results of the plurality of physiological information results.

According to an embodiment, the list of calculation functions comprises autocorrelation function, a Fourier transform function, a Power Spectral Density function; and a Laplace transform.

According to an embodiment, the method further comprises measuring an amplitude of the signal.

According to an embodiment, the method further comprises a measuring a variation in the amplitude of the signal.

According to an embodiment, the method further comprises measuring the angle of a reflected illumination levels from a region of interest.

According to an embodiment, measuring the angle comprises at least one of calculating a histogram of the reflected illumination levels across the region of interest, measuring gradients in the illumination levels across the region of interest and measuring a level of a reflected illumination using a directional photodiode.

In another aspect, there is provided a computer program product comprising instructions which, when carried out on a computer, cause the computer to carry out the method and any variants described herein.

BRIEF DESCRIPTION OF THE DRAWINGS

The above, as well as additional objects, features and advantages of the disclosed devices, systems and methods, will be better understood through the following illustrative and non-limiting detailed description of embodiments of devices and methods, with reference to the appended drawings, in which.

DETAILED DESCRIPTION OF EMBODIMENTS

In the following description, same references designate like elements. Where an element has been described, it is not described again unless further explanation is needed.

Figure 1:
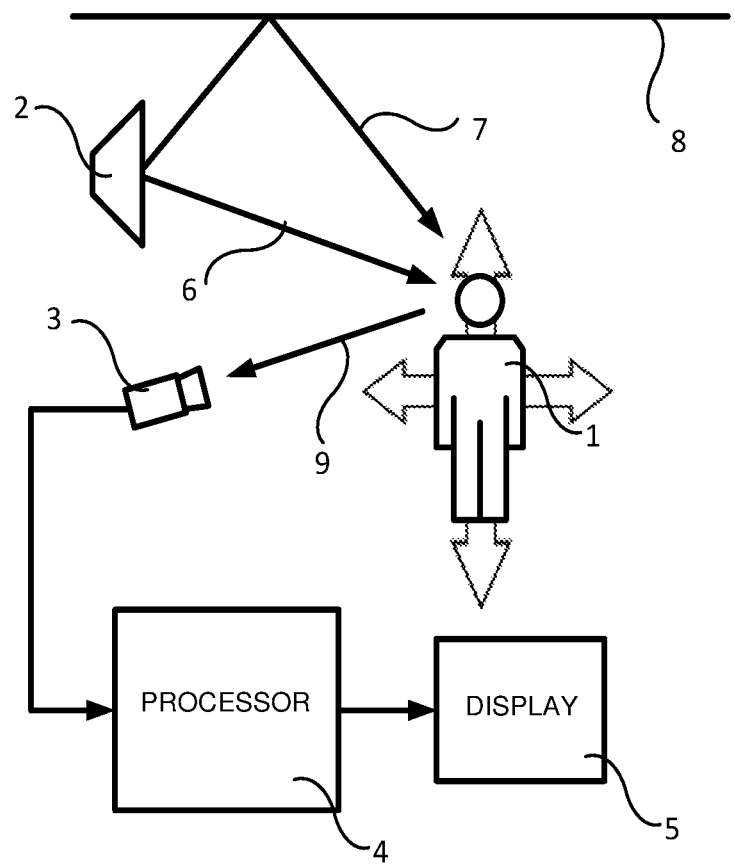
FIG. 1 represents a system for measuring a physiological process in a subject.

FIG. 1 represents an arrangement for capturing and analyzing a sequence of video images from a subject in order to extract information concerning a physiological process occurring in the subject ('physiological information'). A subject 1 is illuminated by a light source 2 and filmed using a camera 3, the camera being setup to capture sequences of video images. The sequence of video images from the camera 3 is fed to a processing device 4 (PROC) which analyses the sequence of video images, extracts a signal from the sequence and from the signal extracts a result, such as a heart-rate. The result, and where desired, a representation of the signal is then provided to a display 5 (DIS).

Some parts of the subject will be better suited for extraction of the signal than others. For example, in the case of blood flow and heart-rate analysis, it has been found that skin areas on the face tend to work better. Therefore it is preferable to select certain areas (Regions of Interest or ROI's for short) or indeed smaller patches contained within these ROIs. Since the signal is composed of changes between frames for a given patch, these patches must be tracked between frames.

The illumination is often directional as opposed to even and as such may take different paths to the subject, depending on the orientation of the light source 2. It may take a direct path 6 from the light source 2 to the subject 1 or it may take an indirect path 7, being reflected from some surface 8 like the ceiling. The light is then reflected along a reflected path 9 to the camera 3. When the light source 2 is aimed at the subject 1, the illumination may arrive on the part of the subject in an approximately even distribution whereas light following the indirect path 7 may arrive at an oblique angle.

As indicated by the arrows shown behind the subject 1, the subject 1 is prone to moving significantly relative to the camera 3, in particular, and to the light source 2 and surface 8. This motion causes two problems. It makes the problem of tracking the patches harder but more importantly, it introduces large variations in the pixel values wherever the tracking is less than perfect.

Since the relative positions of subject 1, light source 2, camera 3 and surface 8 may vary considerably between situations, the intensity and uniformity of the illumination on the subject 1 may also vary considerably. Whilst absolute variations in illumination intensity can, to some degree be compensated, variations in illumination uniformity may have a significant effect on the quality of the signal extraction.

The effects of subject motion and illumination non-uniformity compound each other.

Figure 2:
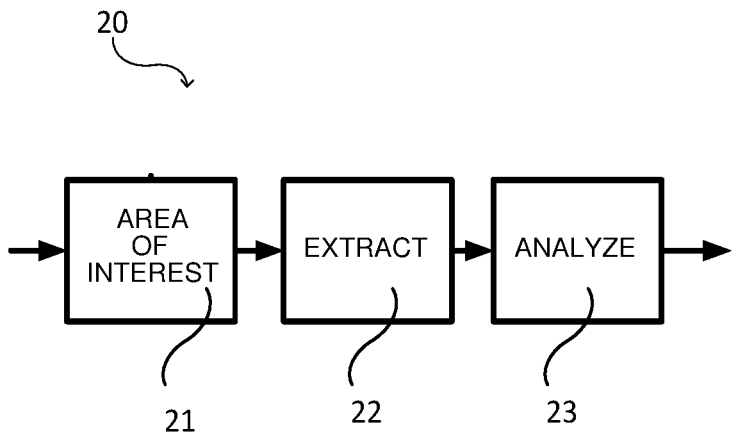
FIG. 2 represents a signal processing chain for extracting physiological information from a sequence of video images.

FIG. 2 represents a processing chain 20 for extracting a signal indicative of a physiological process and from the signal deriving a physiological measurement. The processing chain 20 may be conveniently implemented as part of the processing device 4. A patch selecting unit 21 (ROI) selects the patches or ROIs that are to be tracked. There may be one or more patches which are selected for subsequent processing. The patch selecting unit 21 performs the motion compensation on the images with reference to the selected patches in order to feed a series of motion compensated patches to a signal extractor 22 (EXT). The signal extractor 22 performs operations on the signal in order to arrive at the time-varying signal of interest. These operations may include the combining of the colour channels and/or the normalizing of the signal. It may be that the sequence of patches has been broken up into shorter sequences in order to make the task of motion compensation easier. In this case, the extraction unit 22 may also combine the shorter sequences into longer sequences. The extracted time varying signal is then fed to a signal analyzer 23 (ANA) which, in a role of a physiological information calculator, performs operations in order to arrive at the physiological information result of interest.

The patch selecting unit 21, the signal extracting unit 22 and the signal analyzer 23 may be implemented in a one or more general purpose processors running appropriate software. This has the advantage of being possible with pre-existing hardware and allows for subsequent modification and tuning. However it can result in a solution which is slower and/or more expensive than a mode dedicated solution. Alternatively they may be implemented in microcontrollers running firmware designed to implement the relevant functions. This solution may be less expensive when production volumes are sufficiently high enough. Yet another possibility is to implement the functions in dedicated hardware. In high volumes, this is often cheaper and gives higher processing speed per unit cost.

Figure 3:
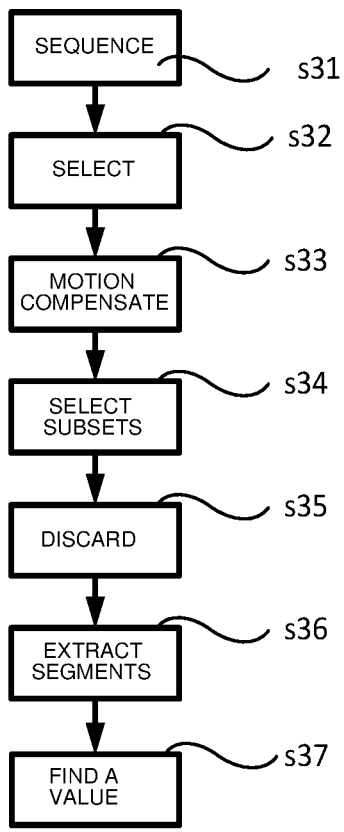
FIG. 3 represents a flow of operations to be performed by the signal processing chain of FIG. 2.

FIG. 3 represents a process applied by the processing chain 20. At step s31 (SEQ), a sequence of frames is provided to the processing chain 20.

At step s32 (SEL), the patch selecting unit 21 selects the patches using one or more of a number of methods. A process which is sometimes called 'segmentation' is performed. It is convenient to start by selecting the general area of interest. The face is suitable whenever blood flow is the physiological process of interest so a face-identification algorithm may be used. A suitable algorithm for implementing face detection is described in Viola, P. and Jones, M. J., "Robust real-time object detection", *Proc. of IEEE workshop on statistical and computational theories of vision*, 13 Jul. 2001. Alternative algorithms for recognizing shape and colour patterns also exist and these may be used for detecting the facial area. For other processes like breathing, other methods for identifying the thorax may be used.

Also the blocks may be classified as being skin areas or not by comparing the relative values of the colours in each pixel therein and absolute intensities of those pixels. Analysis of colour gradients inside and between blocks can also be helpful for identifying skin areas. Identifying skin areas is made more difficult by the wide variety of possible skin tones and account should be taken of this.

At step s33 (MC) a preferable step of motion compensation is performed by the patch selecting unit 21. This is preferable because it is better to perform the signal extraction by taking pixel values from the same area in the series of frames under analysis.

This may be done by the patch selecting unit 21 identifying blocks containing distinctive features within the selected patch(es) and determining how these blocks change position within their respective frames relative to the other frames. Various solutions exist for this. From these changes, the patch selection unit 21 is able to derive predicted motion vectors which it can use to 'align' the selected patch(es) from frame to frame.

It is often useful to select one or more subsets of pixels within the general area of interest. Also it may be that a compromise between processing power requirements, processing time and accuracy is needed and acceptable results can be achieved with fewer pixels.

At step s34 (SUBS), such subsets containing at least one pixel and often contain plurality of pixels are selected by the patch selecting unit 21. The corresponding subsets from all the frames in the sequence are identified to form a group. These corresponding subsets are best matches according a chosen criterion of similarity. Such a criterion could, for example, be based on a statistical measure such as standard deviation of the three colours. Where multiple subsets are being processed in parallel, there will be multiple groups. The process of establishing the groups may be done in various ways. An exhaustive search for similar subsets in the general area of interest may be performed. This can be done by moving a selection window which selects a small set of pixels over the area being searched. Each small set is then compared to a reference small set in a frame being taken as the origin for the purposes of the motion estimation. This is more accurate but computationally expensive. Alternatively at the predicted motion vectors previously derived may least in part, used. This has a lower computational cost but is less accurate. Where a search is performed, fresh predicted motion vectors may be derived. It may also be possible to combine the various approaches in a multiple-stage process, using both searching and predictive motion vectors. Such a solution may be an acceptable compromise between accuracy and computational cost.

Where multiple groups are being used, it is often useful to perform an optional step s35 (DIS) of discarding those groups which do not meet a criterion. This may be performed by the signal extractor 22. The criterion is typically chosen so as to remove groups that will provide an inferior signal extraction result, for example by degrading the overall signal-to-noise ratio. Such criterion could be spatial uniformity of colour and/or texture. Another possibility is the degree of motion between frames in the sequence so that groups exhibiting too much motion between frames could be eliminated.

At step s36 (SEG), the signal extractor 22 builds up extracted signal segments from each group. This is achieved by finding the differences in the pixel values between frames for the group in question. Various preparatory operations are possible. For example, the pixel values in the groups may be normalized i.e. their values may be divided by their average. For example, all the pixel values for a subset may be combined on a per frame basis. This combination may be by finding an average value (weighted appropriately) and the average may have weighting applied between the colour channels. It is possible to combine all of the subsets into a single average i.e. a single average per frame. This has the advantage of robustness to noise. The extracted signal segments may be for short sections of the total sequence of the image frames. This improves the robustness to motion of the subject between frames but may then require further processing to 'reconstruct' the signal over the full sequence of frames.

At step s37 (VAL), the extracted signal segment (or segments) is analyzed by the signal analyzer 33 in order to find a value representing the physiological parameter of interest i.e. the physiological information result. This might be a frequency representation such as a heart or respiration rate or it might relate to an amplitude such as that of the subjects respiration. Indeed it may even be a result derived from one of these.

Situations involving obtaining a frequency will now be discussed.

Such operations could be transforming into a spectrum, i.e. frequency domain, by using something like a Discrete or Fast Fourier Transform (DFT or FFT). From the spectrum the DC component and other components considered out-of-band may be discarded and a peak corresponding to the fundamental frequency of the pertinent physiological process.

A DFT may be expressed as, for a sequence of N complex numbers $x_n$ $$x_k \stackrel{\text{def}}{=} \sum_{n=0}^{N-1} x_n \cdot e^{-j2\pi kn/N}$$

Another method could be to use an autocorrelation (sometimes known as a cross-autocorrelation or serial correlation) function to arrive at result indicative of a quasi-periodic signal. By way of illustration only, a common formation of an estimation for autocorrelation function for a signal for which n observations have been made and for which there are mean $\mu$ and variance $\sigma^2$:

$$\hat{R}(k) = \frac{1}{(n-k)\sigma^2} \sum_{t=1}^{n-k} (X_t - \mu)(X_{t+k} - \mu)$$

where k is an integer less than n.

From the inverse of the time lag between the peaks of the autocorrelation, a frequency of the periodic signal can be derived.

A third method could be to use a power spectral density function (PSDF). This function represents the frequency distribution of the power of a signal. It is sometimes defined or expressed as, for a finite time series $x_n$ of samples of a signal, the samples being at discrete times $x_n = x(n\Delta t)$ for a total time period $T = N\Delta t$:

$$S_{xx}(\omega) = \frac{(\Delta t)^2}{T} \left| \sum_{n=1}^{N} x_n e^{-i\omega n} \right|^2$$

where n is between 1 and N

It may be useful to vary the above expressions or choose different formulations, possibly with other terms, when implementing them in a system for extracting physiological information.

Another possibility is a Laplace transform which can also be used to obtain a frequency-domain representation of a signal from its time-domain form.

Other possibilities exist such as the multiple signal classification (MUSIC) algorithm, the pitch detection algorithm (PDA), the average magnitude different function (ADMF), the average squared mean difference function (ASDMF). There are also algorithms known as the YIN algorithm and the MPM algorithms respectively.

Figure 4:
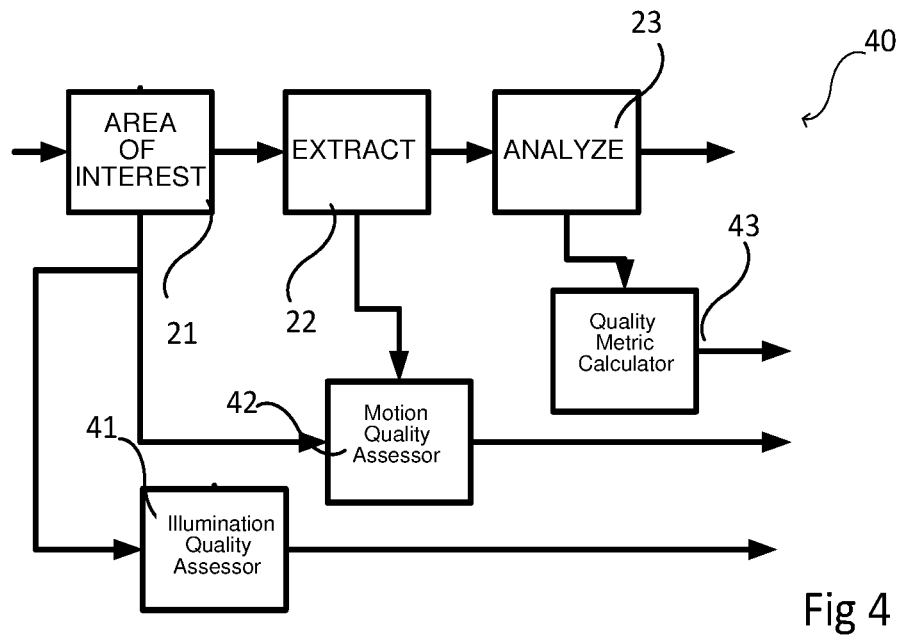
FIG. 4 represents an arrangement according to an embodiment for providing a quality metric from output from the processing chains of FIG. 2.

FIG. 4 represents a system 40 for producing a quality metric according to embodiments. As in FIG. 2, there is a signal processing chain which comprises a patch selecting unit 21, an extraction unit 22 and a signal analyzer 23. In addition to providing a series of motion compensated patches to the extraction unit 23, in one embodiment, the patch selecting unit 21 provides input to an illumination quality assessor (ILL) 41 and to a motion quality assessor (MOT) 42. In another embodiment, the signal extractor 22 provides information to the motion quality assessor 42. The signal analyzer 23, as well as providing a physiological measurement result, gives input to a quality metric calculator (QMC) 43.

Figure 5:
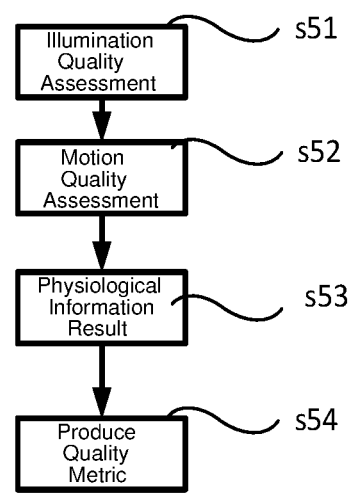
FIG. 5 represents a flow according to an embodiment to be performed by the arrangement of FIG. 4.

FIG. 5 represents a flow operated according to an embodiment by the system of FIG. 4.

At step s51, the patch selection unit 21 provides frames or more particularly, the selected general area of interest, to the illumination quality assessor 41. The illumination quality assessor 41 can use the convenient approach of calculating a histogram of the pixel values for the whole frame or the general area of interest. This may be performed per colour channel or for the colour channels combined. From the histogram(s), representative values such as means, standard deviations, or medians may be combined with values for the quantization noise and the camera noise, to produce a signal-to-noise ratio as dependent on the illumination can be arrived at. The quantization defined by the number of bits used in the pixels to store their values for each colour and the camera noise is defined by camera hardware and is a function of things like the image sensor and the camera optics. Both these parameters can be known for a given system.

At step s52, the patch selection unit 21 provides to the motion compensation assessor 42 information from the processing concerning the motion compensation it performed during step s33. This information can be the related to the predicted motion vectors used in the image stabilization. For example, the maximum magnitude of the predicted motion vectors could be used. The corrections used in motion compensation sometimes introduce errors (sometimes called 'artifacts') into the corrected image. Examples of such artifacts are distortions present near boundaries between strongly contrasting areas. It is possible to search for these artifacts by comparing parameters such as contrast gradients in regions where they might be expected.

In an alternative embodiment, the signal extractor 22 provides information concerning the extracted signals to the motion quality assessor 42. The motion quality assessor can calculate the variations over time in the extracted signal level. In any given situation, the extracted signal level should remain relatively constant or at least within certain boundaries. Variations outside expected limits are often the result of the effects of motion of the subject or of the artifacts introduced by the motion compensation. For example, Motion compensation artefacts may increase and/or decrease pixel-differences between subsequent patches which results in apparent changes in amplitude in the signal for those points in time.

It should be noted that it is possible to combine the above two forms of the motion quality assessor 42 and use both ways of assessing the motion compensation quality.

It is possible to look at local variations at specific times or from specific parts of the image or at average variations over time and compare them to limits or expected values. Furthermore, the signal strength relative to the pixel values, averaged over time, can be expected to be within certain bounds in as much as the general sensitivity of given systems detecting given physiological phenomena can be learned. Therefore excursions outside these bounds can be used to indicate the presence of errors. Therefore, they can be used to assess the degree of subject motion and the efficacy of the motion compensation i.e. as a quality metric for the motion compensation.

At step s53, the signal analyzer 23 performs operations according to an embodiment to derive the physiological information result. As previously mentioned, there are different options for the motion compensation and selecting the area of interest. These have different characteristics and, under certain conditions, any two chosen methods may yield different results. Furthermore the extracted signal will often be weak in comparison to the background pixel values.

In order to extract a frequency value, there are various options, as discussed above. These can also produce differences in the results they produce as a consequence of the effects of the previous steps, particularly since the extracted signal on which they will operate is often relatively weak compared to the absolute pixel values from which it is extracted. For example, with an ACF, it is hoped to produce peaks which can be detected so that the lag between them can be found. Because of the weak signal and the effects of the previous processing steps, the peak detection may be difficult. This can go as far as to produce lags which are longer than the real lag and which are interpreted as an apparent frequency less than the actual value. For a short-time or discrete Fourier transform (STFT or DFT), the low signal-to-noise ratio may result in spurious peaks in the output spectrum and these can make finding the peak of interest more difficult, sometimes to the extent that the apparent fundamental frequency is twice the real value. The Power Spectral Density Function (PSDF) also has sensitivities to certain defects in the extracted signal.

Therefore, at step 54, the two or more methods are used on the same signal and the result compared by the quality metric calculator 43 to produce a quality metric representative of the quality of the results of the time to frequency transformation ("comparison of analysis methods"). The comparison may be performed by finding the difference between the two results. Other possibilities could be to record the differences over a series of time intervals and calculate a variance of the distribution of the differences or to calculate correlation coefficients of the two (or more) populations of readings. Further possibilities may exist.

Thus the system can produce a quality metric for physiological information extraction from a sequence of image frames by using a signal extraction unit to extract the signal and then a signal analyser to calculate a plurality of physiological information results from the signal using a plurality of calculation functions, each result using a different calculation function, and then using a quality metric calculator for calculating a quality metric based on a comparison between the physiological information results of the plurality of physiological information results. This offers the advantage that the degree to which they agree can be an indication of the extracted signal quality, and hence the image processing that contributed to it, can be derived.

Typically the signals extracted from the image frames is a time-domain representation and the physiological information results are frequency-domain or of a form from which a frequency can readily be derived.

The methods may be chosen from amongst autocorrelation function, a Fourier transform and a power spectral density function. Other methods of deriving a frequency exist and may also be used. These have the advantage of having slightly different characteristics and sensitivities. Therefore the degree of agreement may be a useful indication of the quality of the overall process.

Figure 6:
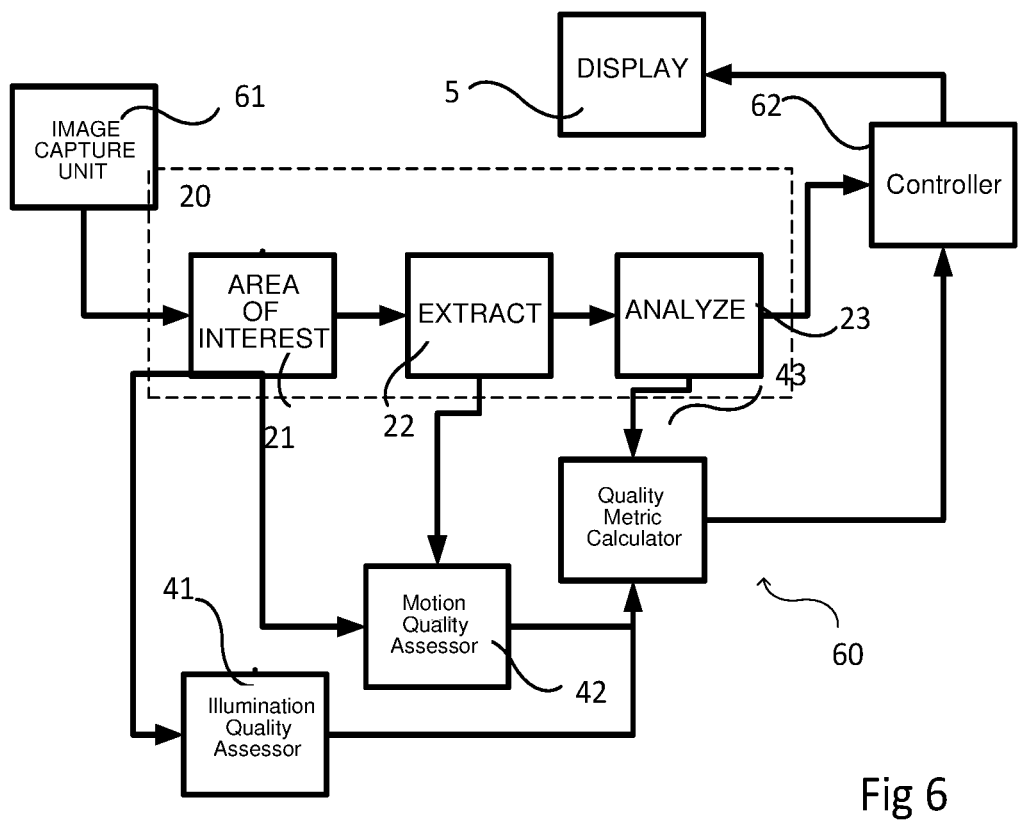
FIG. 6 represents an arrangement according to an embodiment for providing a quality metric from output from the processing chains of FIG. 2, arranged in relation to an image processing system.

FIG. 6 represents a system 60 for producing physiological information comprising a system for producing a quality metric according to an embodiment. An image capture unit 61 (IC) provides a sequence of video frames to a processing chain 20. The physiological information is fed to a controller 62 (CON) which is coupled to a display 5. The illumination quality assessor 41, motion quality assessor 42 receive their inputs from the processing chain 20 as described in relation to FIG. 4. The quality metric calculator 43 receives input, as described above, from the signal analyzer 23 and performs a 'comparison of analysis methods'. The quality metric calculator 43 also receives the results from the illumination quality assessor 41 and the motion quality assessor 42. It provides the quality metric to the display 5. The image capture unit 61 may also provide the sequence of images, or part thereof, to the display. The system 60 may be integrated, wholly or partially, into a single piece of equipment and the single piece of equipment may be the video camera 2 or another equipment such as a computer. The equipment could be implemented in a smartphone.

The display coupled to the controller 62 may display the quality metric as a numerical value, for example a percentage, or a representation on a scale so as to communicate to a user the reliability of the physiological information which is (or has been) displayed. The display could also be a colour representation such as a red-amber-green arrangement. A combination of the above is also possible.

The quality metric could be displayed as it is calculated, possibly with updates made after periods of measurement. Another possibility is for the system 60 to compare the quality metric value against a chosen limit and record whether it is a pass or fail. Over a chosen time period, the system 60 could record the incidence of these pass-fail results and if the incidence itself is below a chosen limit, that time period as a whole could be considered acceptable and reported as such—for example with a green light. Alternatively it could report the percentage of passes as a derived quality metric. For example, the system could record over a two-minute period the number of above/below samples at a rate of one per second. If less than 50% are outside limits, the whole two minutes is acceptable.

The quality metric calculator 43 may combine the result from the illumination quality assessor 41 into the quality metric along with the result of the 'comparison of analysis methods'. This has the advantage that along with the general assessment of the process provided by the 'comparison of analysis methods', the quality metric has sensitivity to the illumination quality and can be used by the user to adjust the illumination.

The quality metric calculator 43 may combine the result from the motion quality assessor 42 into the quality metric along with the result of the 'comparison of analysis methods'. This has the advantage that along with the general assessment of the process provided by the 'comparison of analysis methods', the quality metric has sensitivity to the motion compensation quality. The quality metric could be used either by the user to adjust the system settings or to stabilize the subject, encourage them to move less or limit certain movements like rotation of the head. Another possibility is that the quality metric could be used by the controller 62 to control the settings of the signal extraction unit 22.

The quality metric calculator 43 may combine the various individual quality metrics as a weighted sum. It may check each one individually against limits and add the pass/fail results if a simple display of the quality metric is to be used. It may also calculate a weighted sum of their values outside their respective limits. It could also use the frequency of their excursions outside the limits. Combinations of these methods are also possible. Combining the individual quality metrics has the advantage that as well as an overall assessment of the process, the quality metric also can reflect the problems arising from specific parts of the process such as illumination quality and the motion compensation. The individual quality metrics could also be combined as part of a supervised learning approach.

Illumination homogeneity may have a significant influence on the final result. Therefore it can be desirable to estimate this and either use this estimation as part of the quality metric and/or giving an indication to a person using the system about whether the illumination should be adjusted.

A particular problem occurs when the illumination is directional and arrives at an oblique angle on the general area of interest. Since the general area of interest, such as a face, is often not flat, oblique illumination can cause shadowing or significant, e.g. motion-induced, variation in the level of reflected light across the general area of interest. This effect causes degradation in the signal-to-noise ratio partly because the actual level of illumination on areas selected for signal extraction can be lower or the illumination generally less even than seems to be the case to a user. More importantly the gradients of illumination thereon can interact with the signal processing, particularly the motion compensation and degrade significantly the signal-to-noise ratio. Indeed this phenomenon further amplifies the problems caused by the movement of the subject.

Figure 7:
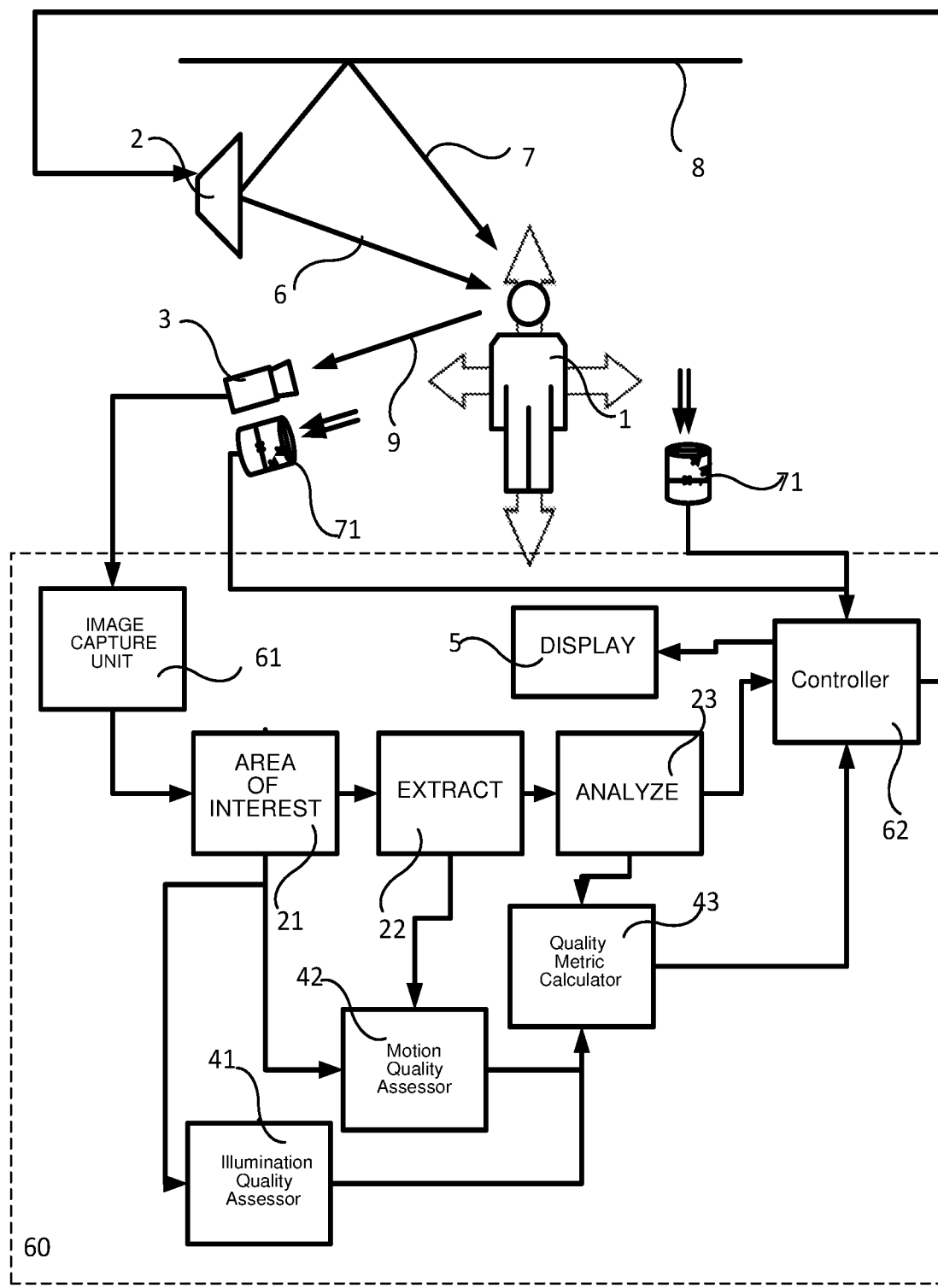
FIG. 7 represents the arrangement of FIG. 6 in relation to a system such as FIG. 1.

FIG. 7 represents an arrangement for capturing and analyzing a sequence of video images from a subject in order to extract information concerning a physiological process occurring in the subject ('physiological information') using a system 60 according to embodiments. In addition to the elements described in relation to FIG. 1 and those of the system 60, photodiodes 71 are arranged so as to receive light from selected directions, i.e. they are directional, and provide results of their measurement of the light incident upon them to controller 62.

The light reflected, or emitted, from the surface 8 often can often exacerbate the difficulties encountered by the motion compensation functions. This is particularly true whenever the surface 8 is a ceiling and whenever the subject 1 is upright because the illumination falls on the face of the subject at a significantly shallow angle. When the light reflected, or emitted, from the ceiling is the dominant source of light, the problem is worse.

The system can measure the degree to which oblique illumination is affecting the results in a number of ways. The system may contribute to an illumination quality metric by using an illumination angle assessor 641 to measure the illumination homogeneity or angle from reflected illumination levels. This has the advantage of being more sensitive to defects or problems that are the result of the set-up or environment of the overall system. The illumination angle assessor may be combined into the aforementioned illumination quality assessor 41.

Thus the illumination angle assessor may use at least one of a histogram of pixel values, measurements of gradients, or standard deviation in said pixel values across the area of interest and a reading from a directional photodiode. The advantages of these is discussed below.

A histogram of the pixel values of pixels distributed across all or part of the general area of interest may reveal a large spread (the spread, or standard deviation, or variance) of values which can be indicative of oblique illumination because such illumination accentuates the shadowing produced by the topography of the subject. This histogram is similar in information content to the one discussed with reference to FIG. 5 and so may be implemented easily as part of the quality metric in a similar manner. It should be noted that Statistical parameters such as standard deviation, or variance can be measured without determining a complete histogram. Such a statistical analysis has the advantage of being part of the image processing necessary for the extraction of the physiological information.

Another possibility is to measure gradients in the intensity of the reflected light across the area of interest. This can be accomplished by searching, in one or more frames, the values of pixels in one or more directions across the general area of interest using filters adapted to reveal the presence of gradients. By 'filter', it is meant here mathematical functions or operations that are performed on the values of one or more pixels and in order to detect or reveal the presence of features of interest. Suitable filters for detecting gradients include Haar-like features and these can be selected and applied to detect vertical and/or horizontal gradients. By using a combination of different Haar-like features, it is possible not only to detect the presence of a gradient but to classify it in terms of direction and degree. The information thus produced can then be combined into the quality metric in accordance with any of ways discussed previously. This may be a more precise indication of the illumination quality than histogram and the advantage of including a more precise is that it can then be used to generate feedback that can instruct the user how to improve the set-up. It is possible, also, to combine both methods i.e. to perform a histogram and to refine the result using gradient detection. It may be possible to economize computation resources necessary for the gradient detection by first classifying and selecting using a histogram.

Another possibility is to use the directional photodiodes 71 to measure the levels of light reflected from the surface 8. A simple approach could be to compare a single measurement to a chosen limit. A more accurate approach could be to compare the measurement from a directional photodiode 71 oriented toward the surface 8 with another detection point. Another detection point could be, for example, either that of a second directional photodiode oriented in the same direction as the camera 3 or indeed with the light levels measured by the camera 3 itself. Many cameras have ambient light sensors or light meters which could be used to provide the function of the second directional photodiode 71. The ratio of the level of light detected by the directional photodiode 71 aimed at the surface versus the other detection point could be compared to one or more selected thresholds so as to provide an indication of the acceptability of the angle of the illumination. Alternatively the ratio could be combined into the overall quality metric as discussed earlier. The advantage of directional photodiodes is that they are relatively inexpensive and can be placed and oriented to take into account the actual situation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer or processing unit. In the device claim enumerating several means, several of these means may be embodied by one and the same item of hardware. The mere fact that certain measures are recited in mutually different dependent claims does not indicate that a combination of these measures cannot be used to advantage.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

Storage media suitable for storing computer program instructions include all forms of nonvolatile memory, including but not limited to EPROM, EEPROM and flash memory devices, magnetic disks such as the internal and external hard disk drives, removable disks and CD-ROM disks. The computer program product may be distributed on such a storage medium, or may be offered for download through any appropriate means such as HTTP, FTP, email or through a server connected to a network such as the Internet.

The invention claimed is:

1. A system, comprising:
   a signal extractor, wherein the signal extractor is configured to receive a sequence of image frames of at least an area of interest of a subject, and to extract a signal representative of a physiological characteristic of the subject from a plurality of the image frames;
   a signal analyzer, wherein the signal analyzer is configured to calculate a plurality of physiological information results from the signal using a plurality of calculation functions, wherein the plurality of calculation functions are included in a list of calculation functions, wherein the physiological information results are calculated using different calculation functions than each other, and
   a quality metric calculator, wherein the quality metric calculator is configured to calculate a quality metric value for the physiological information results based on a signal analysis metric derived from a comparison between the physiological information results,
   wherein the list of calculation functions comprises: an autocorrelation function, a Fourier transform function, a power spectral density function, and a Laplace transform.

2. The system of claim 1, wherein the area of interest is illuminated, and the system further comprises an illumination quality assessor configured to produce an illumination value indicative of an amplitude of the signal in response to the illumination.

3. The system of claim 2, further comprising a motion compensation assessor configured to produce a motion compensation metric derived from at least one of a variation in the amplitude of the signal and from a displacement vector representative of a relative motion of an image feature between image frames in the plurality of image frames.

4. The system of claim 1, wherein the area of interest is illuminated with direct illumination and reflected illumination, and the system further comprises an illumination angle assessor configured to produce an illumination angle metric derived from a measurement of reflected illumination levels.

5. The system of claim 4, wherein the illumination angle metric is based on at least one of a histogram of pixel values in the image frames of the area of interest, a standard deviation of the pixel values in the image frames of the area of interest, a variance of the pixel values in the image frames of the area of interest, measurements of gradients in said pixel values in the image frames across the area of interest, and a reading from one or more directional photodiodes disposed in a vicinity of the subject, wherein each of the photodiodes is arranged to receive light from a selected direction.

6. The system of claim 1, wherein the area of interest is illuminated, and the system is configured to calculate the quality metric value based on a combination of at least two of: the signal analysis metric based on the comparison between the physiological information results, an illumination quality metric indicating a degree to which a quality of the illumination of the area of interest is affecting the quality of the physiological information results, a motion compensation metric indicating a degree to which motion of the subject between the image frames is affecting the quality of the physiological information results, and an illumination angle metric indicating a degree to which oblique illumination is affecting the quality of the physiological information results.

7. The system of claim 1, wherein the system is configured to compare quality metric values to a first chosen limit over a chosen time period and record a pass-fail result and compare the number of pass-fail results in the chosen time period to second chosen limit in order to produce a derived quality metric for the chosen time period.

8. The system of claim 1, wherein the system is configured to provide an indication of a quality of the extracted physiological information.

9. A method of producing a quality metric for an extraction of a physiological information result, the method comprising:
   extracting a signal representative of a physiological characteristic of a subject;
   calculating a plurality of physiological information results from the signal using a plurality of calculation functions, wherein the plurality of calculation functions is included within a list of calculation functions, wherein the physiological information results are calculated using different calculation functions than each other, and calculating a quality metric based on a comparison between the physiological information results, wherein the list of calculation functions comprises: an autocorrelation function, a Fourier transform function, a Power Spectral Density function, and a Laplace transform.

10. The method of claim 9, further comprising measuring an amplitude of the signal.

11. The method of claim 9, further comprising measuring a variation in an amplitude of the signal.

12. The method of claim 10, further comprising illuminating an area of interest in the subject, and measuring an angle of a reflected illumination from the area of interest of the subject.

13. The method of claim 12, wherein measuring the angle comprises at least one of calculating a histogram of the reflected illumination levels across the area of interest, measuring gradients in the illumination levels across the area of interest and measuring a level of a reflected illumination using one or more directional photodiodes disposed in a vicinity of the subject, wherein each of the photodiodes is arranged to receive light from a selected direction.

14. A computer program product comprising a tangible non-transitory media having stored thereon instructions which, when carried out by a processor, cause the processor to carry out the method of claim 9.

* * * * *